(12) United States Patent
Minoda et al.

(10) Patent No.: US 9,057,700 B2
(45) Date of Patent: Jun. 16, 2015

(54) SEPARATION/DETECTION COLUMN AND KIT THEREOF

(75) Inventors: Toshiharu Minoda, Myoko (JP); Isamu Ikeda, Myoko (JP)

(73) Assignee: Daicel Corporation, Osaka-shi, Osaka (JP)

( * ) Notice: Subject to any disclaimer, the term of this patent is extended or adjusted under 35 U.S.C. 154(b) by 73 days.

(21) Appl. No.: 13/703,475

(22) PCT Filed: Jul. 8, 2011

(86) PCT No.: PCT/JP2011/065699
§ 371 (c)(1),
(2), (4) Date: Dec. 11, 2012

(87) PCT Pub. No.: WO2012/005353
PCT Pub. Date: Jan. 12, 2012

(65) Prior Publication Data
US 2013/0089468 A1  Apr. 11, 2013

(30) Foreign Application Priority Data

Jul. 8, 2010 (JP) ................ 2010-155628

(51) Int. Cl.
*G01N 21/75* (2006.01)
*G01N 21/64* (2006.01)
(Continued)

(52) U.S. Cl.
CPC ............. *G01N 21/64* (2013.01); *G01N 30/95* (2013.01); *B01D 15/361* (2013.01);
(Continued)

(58) Field of Classification Search
CPC ...... B01J 20/291; B01J 20/283; B01J 20/286; B01J 20/289; B01J 2220/54; C07B 2200/07; C07B 2200/09; G01N 2030/8877; G01N 30/93; G01N 30/95; B01D 15/08; B01D 15/265; B01D 15/361; B01D 61/007

USPC .................. 422/400, 401, 402, 405
See application file for complete search history.

(56) References Cited

U.S. PATENT DOCUMENTS

2004/0262229 A1  12/2004  Okamoto et al.
2008/0167460 A1   7/2008  Okamoto et al.

FOREIGN PATENT DOCUMENTS

JP  54-145191  11/1979
JP  61-201161   9/1986
(Continued)

OTHER PUBLICATIONS

Kim et al, "Determination of metoprolol enantiomers in human urine by coupled achiral-chiral chromatography" Journal of Pharmaceutical and Biomedical Analysis, 22 (2000) 377-384.*
(Continued)

*Primary Examiner* — Dennis M White
(74) *Attorney, Agent, or Firm* — Flynn, Thiel, Boutell & Tanis, P.C.

(57) ABSTRACT

A separation/detection column that can detect a component separated by a separating agent having an optical responsivity which is the same as that of a component in a sample. The separation/detection column is configured by filling one end of a tube 1, having an ultraviolet transparency, with a first filler that has an ultraviolet responsivity and a separation ability to separate the component in the sample, and by filling the other end of the tube 1 with a second filler that has an ultraviolet responsivity which is different from that of the first filler and does not have the separation ability via a spacer 4 constituted by quartz wool, and moreover by inserting an end cap 5 constituted by quartz wool into the other end of the tube 1.

22 Claims, 2 Drawing Sheets

(51) Int. Cl.
*G01N 30/60* (2006.01)
*G01N 30/02* (2006.01)
*G01N 30/95* (2006.01)
*B01D 15/36* (2006.01)
*B01J 20/286* (2006.01)
*B01J 20/283* (2006.01)
*B01D 15/08* (2006.01)
*B01J 20/291* (2006.01)
*B01D 15/26* (2006.01)
*G01N 30/93* (2006.01)
*B01D 61/00* (2006.01)
*B01J 20/289* (2006.01)
*G01N 30/88* (2006.01)

(52) U.S. Cl.
CPC ........ *C07B 2200/07* (2013.01); *C07B 2200/09* (2013.01); *B01J 20/286* (2013.01); *B01J 20/283* (2013.01); *B01D 15/08* (2013.01); *B01J 20/291* (2013.01); *B01J 2220/54* (2013.01); *B01D 15/265* (2013.01); *G01N 30/93* (2013.01); *B01D 61/007* (2013.01); *B01J 20/289* (2013.01); *G01N 30/6069* (2013.01); *G01N 30/6078* (2013.01); *G01N 30/6082* (2013.01); *G01N 2030/8877* (2013.01); *G01N 30/02* (2013.01); *G01N 21/6428* (2013.01)

(56) References Cited

FOREIGN PATENT DOCUMENTS

| | | | |
|---|---|---|---|
| JP | 62-093660 A | | 4/1987 |
| JP | 62093660 A | * | 4/1987 |
| JP | 2005-017268 | | 1/2005 |

OTHER PUBLICATIONS

RF-10AXL, Shimadzu, Spectrofluorometric Detector for Shimadzu HPLC Systems, p. 1-2.*
International Search Report for PCT/JP2011/065699 (2 pgs.).
Chinese Office Action with English translation dated Aug. 4, 2014 (16 pages).

* cited by examiner

SEPARATION/DETECTION COLUMN AND KIT THEREOF

TECHNICAL FIELD

The present invention relates to a separation/detection column having two stationary phases which are different in both optical responsivity to an ultraviolet ray or a coloring reagent, and ability to separate a component in a sample, and a kit thereof.

BACKGROUND ART

As a means of quickly refining a small amount of a sample, a separation/detection (separation-detection) column (flash tube), which is a polyethylene tube column filled with silica gel impregnated with a fluorescent indicator, is sold commercially. This separation/detection column can easily separate a small amount of a chemical compound in a sample by attaching the sample to the end of the column and filling an eluent into the column. In this separation/detection column, the separation state can be checked by irradiating an ultraviolet ray, and a separated compound can be easily extracted by cutting out the tube. Furthermore, this separation/detection column does not use such an assistant as a fixing agent, unlike the case of a preparative TLC or other stick columns, hence the influence of an assistant on the sample can be prevented.

A known separating agent is a separating agent containing a polysaccharide derivative, such as a polysaccharide phenylcarbamate derivative, which is useful for separating optical isomers, but some separating agents containing a polysaccharide derivative have an ultraviolet responsivity. In the case of the above mentioned separation/detection column, where separation of a compound is checked by irradiating an ultraviolet ray, a separating agent having an ultraviolet responsivity cannot be used, and therefore the above mentioned separation/detection column still must be considered in terms of separation/detection using a separating agent having an ultraviolet responsivity.

SUMMARY OF THE INVENTION

Problems to be Solved by the Invention

It is an object of the present invention to provide a separation/detection column that can detect a component in a sample separated by a separating agent having the same optical responsivity as the component.

Means for Solving the Problem

The present inventors discovered that, in a column tube, a layer of separating agent, that does not have a separation ability to separate the sample and has an ultraviolet responsivity, is connected to the downstream side of a layer of the separating agent that has a different ultraviolet responsivity and separation ability to separate a sample, whereby the component separated by the latter separating agent is detected well, and the present inventors completed the invention.

In other words, the present invention provides a separation/detection column that has columnar or tubular first and second stationary phases having liquid permeability, with ends of the first and second stationary phases being connected so that liquid is permeable, and a moving phase being permeated in the axis direction of the first and second stationary phases, wherein the first stationary phase has a separation ability to separate a component in a sample, and optical responsivity to an ultraviolet ray or a coloring reagent, which is the same as the optical responsivity of this component, and the second stationary phase has an optical responsivity which is different from that of the component.

The present invention also provides the separation/detection column, wherein the second stationary phase does not have the separation ability.

The present invention also provides the separation/detection column, wherein each of the first and second stationary phases is formed of a packed layer formed by particulate filler in a column tube, a columnar body having liquid permeability, or a separating agent layer having liquid permeability, which is formed on a peripheral surface of a columnar or tubular support body not having liquid permeability.

The present invention also provides the separation/detection column, wherein the shape of the columnar body is cylindrical, and the shape of the support body is cylindrical or cylindrical tubular.

The present invention also provides the separation/detection column, wherein the first stationary phase contains a separating agent for optical isomers, and the second stationary phase does not contain a separating agent for optical isomers.

The present invention also provides a separation/detection kit comprising: a column tube having optical transparency; a first particulate filler having a separation ability to separate a component in a sample, and optical responsivity to an ultraviolet ray or a coloring reagent, which is the same as the optical responsivity of this component; and a second particulate filler having optical responsivity which is different from that of the component.

The present invention also provides a separation/detection kit comprising: a column tube; a first particulate filler having a separation ability to separate a component in a sample and optical responsivity to an ultraviolet ray or a coloring reagent, which is the same as the optical responsivity of this component; and one or both of a second cylindrical body and a second thin layer chromatography stick which can be connected to the column tube so that liquid permeates freely, wherein the second cylindrical body has optical responsivity, which is different from that of the component, and liquid permeability, and the second thin layer chromatography stick has a cylindrical or cylindrical tubular support body not having a liquid permeability, and a second separating agent layer which is formed on the peripheral surface of the support body, and has an optical responsivity, which is different from that of the component, and a liquid permeability.

The present invention also provides a separation/detection kit comprising: one or both of a first cylindrical body having a liquid permeability, a separation ability to separate a component in a sample and an optical responsivity to an ultraviolet ray or a coloring reagent, which is the same as the optical responsivity of this component, and a first thin layer chromatography stick having a cylindrical support not having a liquid permeability and a first separating agent layer formed on a peripheral surface of the support body; a column tube that has an optical transparency and that is connected with the first cylindrical body or the first thin layer chromatography stick so that liquid permeates freely; and a second particulate filler having an optical responsivity which is different from that of the component, wherein the first separating agent layer has a separation ability, an optical responsivity same as that of the component, and a liquid permeability.

The present invention also provides a separation/detection kit comprising: one or both of a first columnar body having a liquid permeability, a separation ability to separate a component in a sample and an optical responsivity to an ultraviolet ray or a coloring reagent, which is the same as the optical responsivity of this component, and a first thin layer chromatography stick having a columnar or tubular support body not having a liquid permeability, and a first separating agent layer formed on a peripheral surface of the support body; one or both of a second columnar body having an optical responsivity, which is different from that of the component, and a liquid permeability, and a second thin layer chromatography stick having a columnar or tubular support body not having a liquid permeability and a second separating agent layer formed on the peripheral surface of the support body; and a connecting element that connects the first columnar body or the first thin layer chromatography stick and the second columnar body or the second thin layer chromatography stick so that the liquid permeates freely, wherein the first separating agent layer has the separation ability, optical responsivity, which is the same as that of the component, and liquid permeability, and the second separating agent layer has the optical responsivity, which is different from that of the component, and liquid permeability.

The present invention also provides the separation/detection kit wherein the second filler, the second cylindrical body, the second separating agent layer or the second columnar body does not have the separation ability.

The present invention also provides the separation/detection kit, wherein the shape of the second columnar body is cylindrical, and the shape of the support body is cylindrical or cylindrical tubular.

The present invention also provides the separation/detection kit wherein the first filler, cylindrical body, columnar body or separating agent layer contains a separating agent for optical isomers, and the second filler, cylindrical body, columnar body or separating agent does not contain a separating agent for optical isomers.

The present invention also provides the separation/detection column or the separation/detection kit, wherein the separating agent for optical isomers is a polysaccharide derivative.

The present invention also provides the separation/detection column or the separation/detection kit, wherein the polysaccharide derivative is constituted by a polysaccharide and any of an aromatic ester group, aromatic carbamoyl group and aromatic ether group, which is partially or totally replaced with a hydroxyl group or amino group of the polysaccharide.

Advantageous Effect of the Invention

The present invention can provide a separation/detection column that can detect a component in a sample separated by a separating agent having the same optical responsivity as the component, since the first and second stationary phases are formed.

DESCRIPTION OF THE EMBODIMENTS

Figure 1:
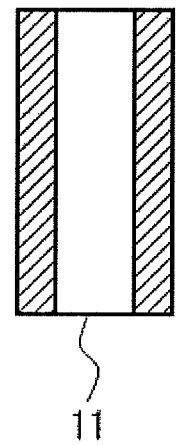
FIG. 1 is a diagram depicting a first example of a connecting element according to the present invention.

A separation/detection column of the present invention has a first and second stationary phases which have a liquid permeability and columnar or tubular shape. Liquid permeability here refers to a characteristic of permeating a liquid from one end to the other end of the stationary phase, while moistening the entire area of the stationary phase in a cross-sectional direction with respect to the axis direction of the stationary phase (entire area of the cross-section of the stationary phase when the stationary phase is sectioned vertical to the axis).

The first stationary phase has an optical responsivity to an ultraviolet ray or a coloring reagent, and a separation ability to separate a component in a sample. Here "optical responsivity to an ultraviolet ray" refers to a light emission, such as fluorescence by an ultraviolet ray, or absorption of an ultraviolet ray. "Optical responsivity to a coloring reagent" refers to the coloring generated by the coloring reagent. "Separation ability to separate a component in a sample" refers to exhibiting different adsorptions for at least two components, out of the components in a sample.

The optical responsivity of the first stationary phase is the same as the optical responsivity of the component in the sample. "Same optical responsivity" here means that one optical responsivity and the other optical responsivity are optically indistinguishable by color or brightness.

The second stationary phase has an optical responsivity which is different from the optical responsivity of the component, that is, the optical responsivity of the first stationary phase. "Different optical responsivity" means that one optical response and the other optical response to the irradiation of an ultraviolet ray or coloring processing by a coloring reagent are different enough to be optically distinguishable by color or brightness. "Difference of optical responsivity to an ultraviolet ray" refers to, for example, emitting light of different colors when an ultraviolet ray is irradiated, emitting light by an ultraviolet ray vs absorbing the ultraviolet ray, emitting light by an ultraviolet ray vs no response to the ultraviolet ray, or absorbing an ultraviolet ray vs no response to the ultraviolet ray. "Difference of optical responsivity to a color reagent" refers to, for example, developing a color by a coloring reagent vs no coloring by the coloring reagent, and different colors developed by a coloring reagent.

Each of the first and second stationary phases can be comprised of a packed layer formed by a particulate filler in a column tube (hereafter called "filled type stationary phase"), a columnar body having a liquid permeability (hereafter called "integrated type stationary phase"), or a separating agent layer having a liquid permeability, which is formed on a peripheral surface of a columnar or tubular support body not having a liquid permeability (hereafter called "thin layer type stationary phase").

The filled type stationary phase can be constructed by filling the filler into a column tube. The filled type stationary phase, as the first stationary phase, can be constructed by filling a first filler, which contains a separating agent having an optical responsivity the same as that of a component in a sample and a separation ability, into the column tube.

For the first filler, particles formed of the separating agent having the optical responsivity and separation ability, particles constituted by particulate carriers having the optical responsivity and a separating agent which is supported by the carrier and has the separation ability, or particles constituted by particulate carriers not having the optical responsivity and a separating agent which is supported by these carriers and has the optical responsivity and separation ability, can be used.

The separating agent has at least the separation ability. If the carriers do not have the optical responsivity, the separating agent has the optical responsivity in addition to the separation ability. An example of a separating agent not having the optical responsivity, such as a separating agent not having the ultraviolet responsivity, is a separating agent not containing an aromatic group. An example of a separating agent having the ultraviolet responsivity is a separating agent containing an aromatic group. The separating agent is properly determined according to the component to be separated in the sample. For example, in the case of separating optical isomers, a separating agent for optical isomers is used for the separating agent.

For the separating agent, both a low molecular separating agent and a high molecular separating agent having the optical responsivity can be used. Examples of the low molecular separating agent are: a ligand exchange type separating agent, a charge transfer (π-π) type separating agent, a hydrogen bond type separating agent, an inclusion type separating agent, an ionic bond type separating agent, an intercalate type separating agent, a crown ether or a derivative thereof, and a cyclodextrin or a derivative thereof. Examples of the high molecular separating agent are: a polysaccharide derivative, a polyamide, a polymethacrylic acid ester, a polyacrylamide, a protein and a tartaric acid derivative.

Various separating agents are known as a separating agent for optical isomers, but a polysaccharide derivative is preferable for its separation performance when versatility is taken into account. This polysaccharide derivative can be a compound constituted by a polysaccharide and one of an aromatic ester group, an aromatic carbamoyl group and an aromatic ether group, which is partially or totally replaced with a hydroxyl group or an amino group of the polysaccharide, and examples of this compound are: a cellulose phenylcarbamate derivative, a cellulose phenylester derivative, an amylose phenylcarbamate derivative, and an amylose phenylester derivative. The phenyl group of these derivatives may have one or more substituent(s) selected from the group consisting of hydrocarbons, of which the carbon number is 1 to 20, and halogen. A specific example of a polysaccharide aromatic ester derivative is cellulose tris(4-methyl benzoate). A specific example of a polysaccharide aromatic carbamoyl derivative is amylose tris(3,5-dimethyl phenylcarbamate). A specific example of a polysaccharide aromatic ether derivative is cellulose tribenzyl ether.

For carriers, a substance not having the separation ability is used. In the case of the first filler, the carrier has the optical responsivity the same as that of the component in the sample, if the separating agent does not have this optical responsivity. An example of a carrier not having the optical responsivity, such as a carrier not having the ultraviolet responsivity, is a carrier not containing an aromatic group, and an example of a carrier having the optical responsivity, such as a carrier having the ultraviolet responsivity, is a carrier containing an aromatic group.

It is preferable to use a porous material for a carrier, in terms of improving the separation performance. The surface of a carrier may be modified in a scope of not having the separation ability. Examples of a carrier are: cross-linked polystyrene, cross-linked acrylic polymer, a synthetic polymer including an epoxy polymer, cellulose and cross-linked cellulose, which is cellulose strengthened by cross-linking, a polysaccharide including cross-linked agarose, cross-linked dextran and cross-linked mannan, and such an inorganic substances as alumina, silica gel, mesoporous silica gel, zeolite, diatomite, fused silica, clay material, zirconia and metal.

The integrated type stationary phase as the first stationary phase can be formed by a first columnar body that has an optical responsivity which is the same as that of the component, liquid permeability and the separation ability. This first columnar body is constituted by a columnar porous material having the separating agent at least on the surface. Such a porous material can be a porous material formed by bonding particles of the first filler filled in the column, a columnar porous material formed by the separating agent, or a columnar porous material formed by the carrier and the separating agent supported thereby.

In the case of a porous material formed by bonding, the particles of the first filler, plastic particles, which are soluble in a solvent in which the first filler cannot be dissolved, and the first filler are mixed, and the obtained mixture is molded by a heat and pressure treatment based on the method disclosed in Japanese Patent Application Publication No. H4-93336, and soluble plastic is removed from the obtained molded body by a solvent treatment. The columnar porous material generated by the separating agent can also be formed using the above mentioned method.

The columnar porous material formed by the carrier can be formed by bonding the carrier particles or by porousifying the columnar body using the carrier. The porous material can be formed by bonding carrier particles using the above mentioned method if the carrier particles are a polymer or such an organic compound as a polysaccharide. The porous material can be formed by porousifying the columnar body by the carrier using the method disclosed in Japanese Patent Publication No. 3397255, and Japanese Patent Publication No. 3317749, that is a sol-gel method.

The separating agent is supported on the columnar porous material by the carrier using a known method, such as the carrier physically absorbing the separating agent, or chemically bonding the separating agent to the carrier, so as to modify or improve the surface of the pores of the porous material.

It is preferable that the columnar body is a cylindrical body in terms of homogenizing the speed of liquid permeation in the entire cross-section of the stationary phase when separation is detected.

The thin layer type stationary phase as the first stationary phase can be formed by the separating agent layer having a liquid permeability, which is formed on the peripheral surface of a columnar or tubular support body not having a liquid permeability. The non-liquid permeability of the support body here refers to a characteristic in which the support body does not permeate the liquid in the entire cross-section of the support body with respect to the axis direction of the support body (entire area of the cross-section of the support body when the support body is sectioned vertical to the axis). Examples of the support body is a columnar body or tube made of glass, metal, synthetic resin or paper treated to be liquid-repellent by attaching a synthetic resin sheet. It is preferable that the support body is cylindrical or cylindrical tubular in terms of easily forming the separating agent at an even thickness, and easily connecting with a stationary phase having a different form.

The separating agent layer is formed on the peripheral surface of the support body. The separating agent layer may be formed on an outer circumference surface or an inner circumference surface of the support body according to the form of the support body. The separating agent layer has a liquid permeability. This separating agent layer can be formed by a layer of the first filler, or a sheet that has the separating agent at least on the surface, and has the liquid permeability. It is preferable that the thickness of the separating agent layer is 0.005 to 5 mm in terms of allowing the moving phase to move at a proper speed upon separation/ detection, it is better if this thickness is 0.01 to 3 mm, and is even better if it is 0.1 to 1 mm. This thin layer type stationary phase can be formed, for example, by coating the slurry of the separating agent containing such other components as a binder on the peripheral surface of the support body, or putting a liquid-permeable sheet having the separating agent on the surface around the peripheral surface of the support body as required.

The filled type stationary phase as the second stationary phase can be formed by filling a second filler, that has an optical responsivity which is different from that of the first stationary phase, into a column tube. A particulate separating agent of which the optical responsivity is different from the separating agent in the first stationary phase, out of the above mentioned separating agents, or a particulate carrier, can be used for the second filler. The integrated type stationary phase as the second stationary phase can be formed by a second columnar body which has an optical responsivity, which is different from that of the first stationary phase, and a liquid permeability. The second columnar body can be formed in the same manner as the first columnar body, except that the separating agent of which the optical responsivity is different from that of the separating agent of the first stationary phase is used, and can be constituted by a columnar porous material by the carrier. The thin film layer type stationary phase as the second stationary phase can be formed by forming a liquid permeable layer having an optical responsivity which is different from that of the first stationary phase, on the peripheral surface of the support body. This layer can be formed, for example, by coating a particulate separating agent, of which the optical responsivity is different from that of the separating agent in the first stationary phase, on the peripheral surface of the support body, coating the slurry of the carrier on the peripheral surface of the support body, or putting a liquid-permeable sheet not having the separating agent around the peripheral surface of the support body.

The secondary stationary phase may or may not have the separation ability. In terms of allowing further separation of the component in the second stationary phase, it is preferable that the second stationary phase has the separation ability, because for example, further analysis of the spot of a desired component from the first stationary phase can be performed, an extraction operation after the second stationary phase is removed, and analysis thereafter can be easier. In terms of accurately detecting the separation state in the first stationary phase, it is preferable that the second stationary phase does not have the separation ability, because for example, detection and preparative isolation of a component separated in the first stationary phase and an accurate measurement of the Rf value of the separating agent in the first stationary phase become easier.

In terms of checking the spot in the second stationary phase, it is preferable that the second stationary phase does not have an optical responsivity, and it is further preferable that the second stationary phase has an optical responsivity that is strikingly different from the optical responsivity of a component in the sample or that of the first stationary phase. For example, if the first stationary phase contains the separating agent for optical isomers, it is preferable that the second stationary phase does not contain the separating agent for optical isomers, and if the component or the stationary phase of the first stationary phase absorbs an ultraviolet ray, it is preferable that the second stationary phase does not have a responsivity to an ultraviolet ray, and emits light by being irradiated by an ultraviolet ray. The second stationary phase of which the optical characteristic has been adjusted in this matter can be formed, for example, by coating a fluorescent agent, which emits a fluorescence by being irradiated by an ultraviolet ray, on a stationary phase which does not have an ultraviolet responsivity.

The column tube may or may not have an optical transparency if only the first stationary phase is included. The optical transparency here refers to a transparency that allows the checking of the optical characteristics (such as coloring, light emission, absorbance) of the spot on the second stationary phase. The column tube has an optical transparency if the second stationary phase is included.

In terms of observing the state during the separation operation, such as the position and state of the moving phase, and the state of the spot, it is preferable that the column tube has a transparency that allows the checking of at least these states. For this column tube, a quartz glass tube and a tube made from a fluororesin, such as PFA (tetrafluoroethylene-perfluoroalkyl vinylether copolymer) can be used. The column tube may have a thickness that functions as a lens in the axis direction, and this column tube which magnifies the spot is preferable in terms of making a visual observation of the spot easier.

The length of the column tube should be a length with which the separation ability of the filler is properly expressed, and in terms of observing the separation of the component, it is preferable that the column tube is long, but in terms of easy handling and an easy detection/separation operation, it is preferable that the column tube is short. As a consequence, it is preferable that the length of the column tube used for the first or second stationary phase is 2 to 50 cm, it is better if this length is 3 to 30 cm, and is even better if it is 3 to 20 cm.

In terms of quickly separating the component, it is preferable that the column tube is thin, and in terms of easily detecting the component and preparative isolation thereof, it is preferable that the column tube is thick. As a consequence, it is preferable that the inner diameter of the column tube is 0.1 to 10 mm, it is better if this inner diameter is 0.1 to 8 mm, and is even better if it is 0.1 to 5 mm.

In terms of separating the component, it is preferable that the particle diameter of the filler is small, and in terms of quickly separating the component, it is preferable that the particle diameter of the component is large. As a consequence, it is preferable that the particle diameter of the filler is 0.5 to 50 µm, it is better if the particle diameter is 1 to 30 µm, and is even better if it is 1 to 20 µm. The particle diameter of the filler can simply be a value that represents a size of a particle of the filler, and may be an average particle diameter or may be a catalog value. The particle diameter of the filler can be determined, for example, by a laser diffraction method and a scattering method.

An end of the first and that of the second stationary phases are connected to each other so that liquid permeates freely. "Liquid permeates freely" refers to liquid permeating from the first stationary phase to the second stationary phase in the entire cross-section of the stationary phase in the axis direction (cross-section of the stationary phase that vertically intersects the axis of the stationary phase). The first and second stationary phases may be directly connected, or may be connected via a connecting element for connecting both of the stationary phases so that a liquid permeates freely, or may be connected via a spacer which has a liquid permeability. Each of the first and second stationary phases may be the above mentioned filled type stationary phase, or an integrated stationary phase or a thin layer type stationary phase.

If the first and second stationary phases are the filled type stationary phases, this separation/detection column can be comprised of a column tube having an optical transparency, a filler which contains the separating agent and is filled into one end of the column tube, and a filler or particulate carrier which does not contain the separating agent, and is filled into the other end of the column tube. It is preferable to dispose the spacer at the center of the column tube. Examples of this spacer are particles that are coarser than the filler, such as absorbent cotton, a fibrin clot (e.g. glass wool), filter paper, glass filter and sea sand.

If one of the first and second stationary phases is the filled type stationary phase and the other is the integrated stationary phase, this separation/detection column can be formed by connecting the column tube forming the filled type stationary phase with the integrated type stationary phase directly or via the spacer or via the connecting element. To directly connect the filled-type stationary phase and the integrated type stationary phase, the integrated type stationary phase is inserted into one end of the column tube of the filled type stationary phase, for example.

Examples of the connecting element are a connecting element which inter-fits with both the end of the first stationary phase and the end of the second stationary phase, or an adhesive material which is put around the outer circumferential surfaces of one end of the first stationary phase and one end of the second stationary phase.

Figure 2:
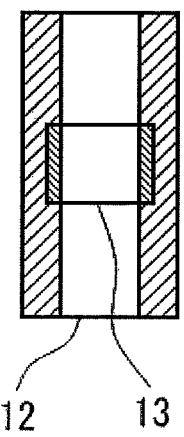
FIG. 2 is a diagram depicting a second example of the connecting element according to the present invention.
Figure 3:
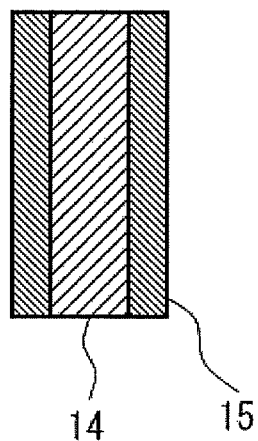
FIG. 3 is a diagram depicting a third example of the connecting element according to the present invention.

Examples of the connecting tube are: a connecting element constituted by a synthetic resin circular tube 11 that does not have a liquid permeability and is externally inserted into an end of the first stationary phase and an end of the second stationary phase as shown in FIG. 1, a connecting element constituted by a circular tube 12 that does not have a liquid permeability and is externally inserted into an end of the first stationary phase and an end of the second stationary phase, and a liquid permeating material 13, such as ceramic paper or glass wool, which is disposed at the center portion of the inner circumferential surface of the circular tube 12, as shown in FIG. 2, and a connecting element constituted by a non-liquid permeable cylindrical body 14 and a liquid permeable material 15 coating the outer circumferential surface of the cylindrical body 14 so as to be internally inserted into the column tube or cylindrical tubular support body, as shown in FIG. 3.

The connecting element in FIG. 1 can be suitably used for connecting filled type stationary phases, connecting integrated type stationary phases, or connecting a filled type stationary phase and an integrated type stationary phase. The connecting element in FIG. 2 can be suitably used for connecting thin layer type stationary phases, each of which has a separating agent layer on the outer circumferential surface of the support body, or connecting this thin layer type stationary phase and another type of stationary phase. The connecting element in FIG. 3 can be suitably used for connecting thin layer type stationary phases, each of which has a separating agent layer on the inner circumferential surface of a cylindrical tubular support body, or connecting this thin layer type stationary phase and a filled type stationary phase.

The illustrated connecting elements all have either a cylindrical tubular or cylindrical shape, but may have a cross-sectional shape that is not a circle but matches the cross-sectional shape of the integrated type stationary phase or the filled type stationary shape, or may have a tubular or columnar form of which the cross-sectional shape at one end is a circle and a cross-sectional shape at the other end is not a circle, such as a polygon.

If one of the first and second stationary phases is a filled type stationary phase and the other is the thin layer type stationary phase, this separation/detection column can be formed by directly connecting the column tube forming the filled type stationary phase and the support body having a separating agent layer constituting the thin layer stationary phase, or via the spacer or via the connecting element, just like the case of connecting the filled type stationary phase and the integrated type stationary phase.

If the first and second stationary phases are both the integrated type stationary phase, the separation/detection column can be formed by connecting the respective integrated type stationary phases constituting the first and second stationary phases via the connecting element. These integrated type stationary phases may be inserted into a column tube and be directly connected in the column tube, or be connected via the spacer.

If one of the first and second stationary phases is the integrated type stationary phase and the other is the thin layer type stationary phase, the separation/detection column can be formed by connecting the integrated type stationary phase and the support body having the separating agent layer constituting the thin layer stationary phase directly or via the connecting element.

If the first and second stationary phases are both the thin layer stationary phases, the separation/detection column can be formed by forming a liquid permeable first separating agent layer containing the separating agent on one end of the peripheral surface of the support body, and forming a liquid permeable second separating agent layer constituted by a filler which does not contain the separating agent or the particulate carrier, on the other end of the peripheral surface of the support body, adjacent to the first separating agent layer.

If the first and second stationary phases are both filled type stationary phases or both thin layer type stationary phases, this separation/detection column can also be formed by forming the first stationary phase using a first column tube or a first support body, forming the second stationary phase using a second column tube or a second support body, and connecting the respective column tubes or support bodies via the connecting element respectively.

If the first and second stationary phases are both thin layer type stationary phases, the separation/detection column can also be formed by using a columnar support body for one of the support bodies of the first and second stationary phases, and using a tubular support body, which is externally inserted into the columnar support body, for the other support body, and directly connecting these support bodies if a separating agent layer is formed on the inner circumferential surface of the tubular support body.

The length of the first stationary phase and the length of the second stationary phase can be the same or different only if the separation ability is properly expressed in each stationary phase. It is sufficient if the first stationary phase has a length that is enough for separating the compound, and the second stationary phase has a length that is enough for detecting the component. For example, it is preferable that the length of the first stationary phase is 1 to 40 cm, and it is better if the length is 1.5 to 25 cm, and is even better if it is 2 to 18 cm. It is preferable that the length of the second stationary phase is 1 to 40 cm, and it is better if the length is 1.5 to 25 cm, and is even better if it is 2 to 18 cm.

In the separation/detection column of the present invention, a moving phase is fed to the first and second stationary phases in the axis direction. The separation/detection column of the present invention can be used for separating an element in a sample, by attaching the sample at one end of the first stationary phase, drying the attached sample as required, feeding the moving phase from one end of the first stationary phase to the other end of the second stationary phase so as to separate components in the sample by the first stationary phase, and allowing at least one of the separated components to reach the second stationary phase, or further separating the component in the second stationary phase. The separation/detection column of the present invention can also be used for detecting the component which reached the second stationary phase by irradiating an ultraviolet ray onto the second stationary phase, or by performing coloring processing using a coloring reagent. The separation/detection column of the present invention can also be used for preparative isolation of the component which reached the second stationary phase by extracting a part or all of the second stationary phase containing the component which reached the second stationary phase, and extracting the component as required.

Water, salt solution, organic solvent or a mixed solvent thereof can be used for the moving phase. One or more types of organic solvent can be used. Examples of salt are a copper sulfate solution or a perchlorate. Alcohol, such as methanol, ethanol and isopropanol, or a hydrocarbon, such as hexane, can be used for the organic solvent. An appropriate amount of acid and alkali can be mixed for the moving phase. Acetic acid, propionic acid and tetrafluoroacetate acid, for example, can be used for the acid in terms of stabilizing a component to be detected, and diethylamine, monoethanolamine and triethylamine, for example, can be used for the alkali.

In the case of detecting the component in the second stationary phase by the optical responsivity using a coloring reagent, a known technology can be used for the coloring reagent and coloring processing thereof. Examples of the coloring reagent are an anisaldehyde solution, a phosphomolybdic acid solution, iodine, a ninhydrin solution, a chameleon solution, a DNPH solution, a manganese chloride solution, and a Bromocresol green solution. An example of the coloring processing is processing of the coloring reagent adhering to the second stationary phase by coating, spraying or exposure, and heating the second stationary phase as required to develop color.

In the separation/detection column of the present invention, it is preferable that the first and second stationary phases are cylindrical or cylindrical tubular in terms of homogeneous liquid permeation of the moving phase in the axis direction of the stationary phase. In the case of the filled type stationary phase, the stationary phase, which allows homogeneous liquid permeation like this, can be easily formed by filling the filler by tapping, immersion of the porous material in the separating agent solution, or by coating the slurry of the separating agent on the support body.

In the case of the filled type stationary phase or the integrated type stationary phase of a porous material constituted by forming an open-cell foam in a cylindrical body of a separating agent or a carrier, the stationary phase can be formed without using an assistant that is required for forming a phase, such as a binder using for forming a separation layer in the thin layer chromatography plate, hence the influence of an assistant on separation can be prevented. This stationary phase is also easy to be formed and used for other detection/separation apparatuses, such as a thin layer chromatography plate, therefore it excels in operability.

The present invention includes a kit that can construct the above mentioned separation/detection column of the present invention. This separation/detection kit may be a separation/detection kit that includes: the column tube having an optical transparency; the first filler having a separation ability to separate a component in a sample and an optical responsivity which is the same as that of the component; and the second filler that has an optical responsivity, which is different from that of the first separating agent, and may have the separation ability. In this separation/detection kit, the separation/detection column of the present invention is formed by filling the first filler into one end of the column, and filling the second filler into the other end of the column, so as to be adjacent to the first filler layer or via the spacer. Since the separation/detection kit can freely set the type of the filler and the length of the stationary phase for the separation/detection column, this separation/detection kit is effective when considering separation conditions.

The separation/detection kit may also be a separation/detection kit that includes the column tube, the first filler, and one or both of the second cylindrical body and the second thin layer chromatography stick, which are connected to the column tube so that liquid permeates freely. The second cylindrical body is the integrated type stationary phase that has an optical responsivity, which is different from the optical responsivity of the first filler, and may have the separation ability. The second thin layer chromatography stick has a columnar or tubular support body not having a liquid permeability, and a separating agent layer formed on the outer circumference surface or the inner circumference surface of this support body, where this separating agent layer is an element that has an optical responsivity, which is different from the optical responsivity of the first filler, and may have the separation ability, and constitutes the thin layer stationary phase. In this separation/detection kit, the first stationary phase can be formed by filling the first filler into the column tube. The separation/detection column of the present invention can be formed by inserting the second cylindrical body or the second thin layer chromatography stick into the end of the column tube. Since this separation/detection kit can freely set the type of the first filler for the separation/detection column, and easily connect the first stationary phase and the second stationary phase, this separation/detection kit can be effectively utilized for such as consideration of the separation conditions.

The thin layer chromatography stick includes a form of a columnar or tubular support body where the separating agent layer is formed on the outer circumferential surface, and a form of a tubular support body where the separating agent layer is formed on the inner circumferential surface. For the columnar support body, a stick of which the cross-sectional shape is a polygon or a circle, can be used, for example, and for the tubular support body, a tube of which the cross-sectional shape is a polygon, a column tube, or a tube having the same dimensions as the column tube, for example, can be used.

The separation/detection kit may be a separation/detection kit that includes one or both of a first cylindrical body and a first thin layer chromatography stick, a column tube having an optical transparency which is connected to the first cylindrical body and/or the first thin layer chromatography stick so that liquid permeates freely, and the second filler. The first cylindrical body is the integrated type stationary phase that has a liquid permeability, has the separation ability to separate a component in a sample, and has an optical responsivity, which is the same as the optical responsivity of the component. The first thin layer chromatography stick has the support body and the separating agent layer which is formed on the outer circumferential surface or the inner circumferential surface of the support body, where the separating agent layer is an element having the liquid permeability, the separation function to separate a component in a sample, and an optical responsivity which is the same as the optical responsivity of the component, and constitutes the thin layer type stationary phase. In this separation/detection kit, the second stationary phase can be formed by filling the second filler into the column tube. The separation/detection column of the present invention can be formed by inserting the first cylindrical body or the first thin layer chromatography stick into the end of the column tube. This separation/detection kit is effective for preparative isolation of the element, for example, since the second stationary phase is the filled type stationary phase in the separation/detection column, and the portion of the stationary phase including an arbitrary spot, can be extracted as a particulate filler.

The separation/detection kit may be a separation/detection kit that includes one or both of the first columnar body and the first thin layer chromatography stick, one or both of the second columnar body and the second thin layer chromatography stick, and the connecting element that connects the first columnar body or the first thin layer chromatography stick and the second columnar body or the second thin layer chromatography stick so that the liquid permeates freely. In this separation/detection kit, the separation/detection column of the present invention can be formed by connecting the first columnar body or the first thin layer chromatography stick and the second columnar body or the second thin layer chromatography stick. This separation/detection kit is effective to detect separation easily, since the first and second stationary phases can be easily connected in the separation/detection column.

The separation/detection kit may be a separation/detection kit that includes: a first column tube which need not have an optical transparency; the first filler; a second column tube which has an optical transparency; the second filler; and a connecting element that connects these column tubes so that the liquid permeates freely. In this separation/detection kit, the separation/detection column of the present invention can be formed by connecting the first column tube in which the first filler is filled and the second column tube in which the second filler is filled, via a connecting element. This separation/detection kit can form each stationary phase in one column tube for a plurality of times, by refilling the filler, and can easily connect these stationary phases, therefore it is very effective in terms of easily forming each filled type stationary phase, and controlling the generation of waste after the separation/detection column is used.

The separation/detection kit may include: a cylindrical or cylindrical tubular stationary phase; a columnar or tubular stationary phase of which the cross-sectional shape is a non-circle, such as a polygon; and a connecting element which connects these stationary phases so that the liquid permeates freely. This separation/detection kit can form a separation/detection column in which stationary phases having different cross-sectional shapes are connected. The stationary phase, of which the cross-sectional shape is a non-circle, is formed by pressurizing the side face of the cylindrical tubular column, which is formed by filling the filler into a column tube, for example. The column, of which the cross-sectional shape is an ellipse, can increase the filling density and make filling uniform, which is preferable in terms of further improvement of the separation ability, and the stationary phase, of which the cross-sectional shape is an ellipse or a rectangle, is preferable in terms of easily generating a capillary phenomenon, decreasing the amount of the filler to be filled, and making a visual observation of the spot from the side face easier. This separation/detection kit can form a separation/detection column that has a stationary phase having the above-mentioned advantages for one of the stationary phases.

The separation/detection kit may include composing elements of a plurality of kits as one kit. The separation/detection kit may include other composing elements that are useful for constructing and using the separation/detection column. Examples of these other elements are: the above-mentioned connecting element, an end cap of a column tube, a tube fitting that connects a column tube and a tube of the moving phase, a stand of the separation/detection column, a container that houses the separation/detection column and the moving phase upon separation/detection, and the above mentioned spacer that is inserted into the column tube or the connecting element as required.

The separation/detection kit may include two or more types of fillers, cylindrical bodies, columnar bodies and thin layer chromatography sticks of which the separating agents are different, and may include two or more types of column tubes, cylindrical bodies, columnar bodies and thin layer chromatography sticks of which the size, material and physical property are different. This separation/detection kit is very effective in terms of considering the separation conditions of the separation/detection column.

EXAMPLES

An example of the present invention will now be described, but the present invention is not limited to the following example.

Figure 4:
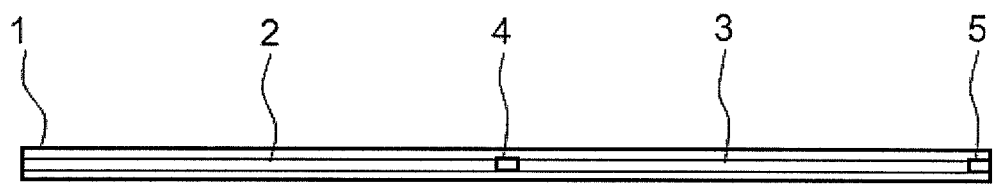
FIG. 4 is a diagram depicting a separation/detection column used for an embodiment of the present invention.

FIG. 4 shows a separation/detection column according to the present example.

The separation/detection column in FIG. 4 comprises a tube 1 having an ultraviolet transparency, a first filler layer 2 which is filled in one end of the tube 1, a second filler layer 3 which is filled in the other end of the tube 1, a spacer 4 which is disposed between the first and second filler layers 2 and 3, and has a liquid permeability, and an end cap 5 which plugs into the other end of the tube 1.

The tube 1 is made from polytetrafluoroethylene. The outer diameter of the tube 1 is 3 mm, the inner diameter of the tube 1 is 1 mm, and the length of the tube 1 is 6 cm.

The first filler layer 2 is a layer of Chiralpak® AD (registered trademark of Daicel Chemical Industries, Ltd.) made by Daicel Chemical Industries, Ltd. (hereafter called "AD filler"). The particle diameter of the AD filler is 20 μm. The filler length of the first filler layer 2 is 3 cm.

The second filler layer 3 is a layer of silica gel. This silica gel contains manganese-containing zinc silicate as the fluorescent agent. The particle diameter of the silica gel is 15 μm. The filling length of the second filler layer 3 is 3 cm.

The spacer 4 and the end cap 5 are made of quartz wool respectively. The filling length of the spacer 4 is 4 mm.

The separation/detection column in FIG. 4 is formed by plugging the end cap 5 into the other end of the tube 1, filling the silica gel from the one end of the tube 1 by tapping, inserting the spacer 4 from the one end of the tube 1 to stop the one end side of the second filler layer, and filling the AD filler from the one end of the tube 1 by tapping until reaching one end of the tube 1.

The sample solution adheres to the one end of the tube 1, that is, the one end of the first filler layer 2. The sample solution is a trans-stilbene oxide (t-SO) solution. The solvent of this sample solution is a mixed solvent containing n-hexane and isopropyl alcohol at a 1:9 volume ratio, and the concentration of the sample is 10,000 mass ppm. The adhesion of the sample solution is performed by directly immersing the one end of the separation/detection column in the sample solution. The adhesion of the sample solution may be performed by dripping the sample solution from the one end of the separation/detection column into the first filler layer 2 using a Pasteur pipette, for example.

Then approximately 0.05 mL of developer (moving phase) is dripped from the one end of the separation/detection column into the first filler layer 2, so that the developer infiltrates into the first filler layer 2. The developer is a mixed-solvent containing n-hexane and isopropyl alcohol at a 9:1 volume ratio. After infiltration, the separation/detection column is placed in the container containing the developer, so that the one end of the separation/detection column is immersed in the developer, and the sample is developed in the first and second filler layers 2 and 3.

Figure 5:
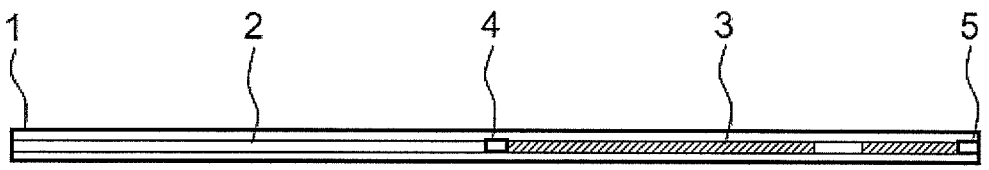
FIG. 5 is a diagram depicting a state where a raffinate component is detected by optical separation of t-SO using the separation/detection column in FIG. 4.

By developing the developer until reaching the end cap 5 by a capillary phenomenon, and irradiating an ultraviolet ray onto the second filler layer 3, fluorescence is observed as shown by the shaded portion in FIG. 5, and a spot of a raffinate component of t-SO (component hardly absorbed by the AD filler), separated by the first filler layer 2, is observed as an area where fluorescence is not emitted.

INDUSTRIAL APPLICABILITY

Recently the further development of effective pharmaceutical components and useful optical isomers as a material thereof is demanded, and the development of technologies to check optical isomers and separate optical isomers more accurately is also demanded. According to the present invention, optical separation by a separating agent having an ultraviolet responsivity, such as a separating agent for optical isomers using a polysaccharide derivate, can be easily performed using column chromatography, and useful material for initial setting and optimization of liquid chromatography conditions can be easily provided. Therefore, because of the present invention, further development of technologies that involve separation by chromatography, such as the development of more useful optical isomers and establishing a more productive manufacturing method for optical isomers, can be expected.

EXPLANATION OF REFERENCE NUMERALS

1 tube
2 first filler layer
3 second filler layer
4 spacer
5 end cap
11, 12 circular tube
13, 15 liquid-permeating material
14 cylindrical body

The invention claimed is:

1. A separation/detection column comprising columnar or tubular first and second stationary phases having a liquid permeability, with ends of the first and second stationary phases connected to each other so that a liquid is permeable therethrough, and a moving phase permeates in the axis direction of the first and second stationary phases, wherein
the first stationary phase has a separation ability to separate a component in a sample and an optical responsivity to an ultraviolet ray or a coloring reagent, which is the same as the optical responsivity of the component, and
the second stationary phase has an optical responsivity which is different from that of the component.

2. The separation/detection column according to claim 1, wherein the second stationary phase does not have the separation ability.

3. The separation/detection column according to claim 1, wherein each of the first and second stationary phases is formed of a packed layer formed by particulate filler in a column tube, a columnar body having a liquid permeability, or a separating agent layer having a liquid permeability, which is formed on a peripheral surface of a columnar or tubular support body not having a liquid permeability.

4. The separation/detection column according to claim 3, wherein the shape of the columnar body is cylindrical, and the shape of the support body is cylindrical or cylindrical tubular.

5. The separation/detection column according to claim 1, wherein the first stationary phase contains a separating agent for optical isomers, and the second stationary phase does not contain a separating agent for optical isomers.

6. The separation/detection column according to claim 5, wherein the separating agent for optical isomers is a polysaccharide derivative.

7. The separation/detection column according to claim 6, wherein the polysaccharide derivative is constituted by a polysaccharide and any of an aromatic ester group, aromatic carbamoyl group and aromatic ether group, which is partially or totally replaced with a hydroxyl group or an amino group of the polysaccharide.

8. A separation/detection kit comprising:
a column tube having optical transparency;
a first particulate filler having a separation ability to separate a component in a sample and an optical responsivity to an ultraviolet ray or a coloring reagent, which is the same as the optical responsivity of the component; and
a second particulate filler having an optical responsivity which is different from that of the component.

9. The separation/detection kit according to claim 8, wherein the second filler does not have the separation ability.

10. The separation/detection kit according to claim 9, wherein the first filler contains a separating agent for optical isomers and the second filler does not contain a separating agent for optical isomers.

11. A separation/detection kit comprising:
a column tube;
a particulate filler having a separation ability to separate a component in a sample and an optical responsivity to an ultraviolet ray or a coloring reagent, which is the same as the optical responsivity of the component; and
one or both of a cylindrical body and a thin layer chromatography stick which can be connected to the column tube so that liquid permeates freely, wherein
the cylindrical body having an optical responsivity which is different from that of the component and a liquid permeability, and
the thin layer chromatography stick has a cylindrical or cylindrical tubular support body not having a liquid permeability, and a separating agent layer, which is formed on the peripheral surface of the support body, has an optical responsivity which is different from that of the component and a liquid permeability.

12. The separation/detection kit according to claim 11, wherein the cylindrical body and the separating agent layer do not have the separation ability.

13. The separation/detection kit according to claim 12, wherein the particulate filler contains a separating agent for optical isomers and the separating agent layer does not contain a separating agent for optical isomers.

14. A separation/detection kit, comprising:
one or both of a cylindrical body having a liquid permeability, a separation ability to separate a component in a sample and an optical responsivity to an ultraviolet ray or a coloring reagent which is the same as the optical responsivity of the component, and a thin layer chromatography stick having a cylindrical support not having a liquid permeability and a separating agent layer formed on a peripheral surface of the support body;

a column tube that has an optical transparency and is connected with the cylindrical body or the thin layer chromatography stick so that a liquid permeates freely therethrough; and a particulate filler having an optical responsivity which is different from that of the component, wherein the separating agent layer has a separation ability and optical responsivity the same as that of the component, and a liquid permeability.

15. The separation/detection kit according to claim 14, wherein the particulate filler does not have the separation ability.

16. The separation/detection kit according to claim 15, wherein the cylindrical body and the separating agent layer contain a separating agent for optical isomers and the particulate filler does not contain a separating agent for optical isomers.

17. A separation/detection kit, comprising:
one or both of a first columnar body having a liquid permeability, a separation ability to separate a component in a sample and an optical responsivity to an ultraviolet ray or a coloring reagent, which is the same as the optical responsivity of the component, and a first thin layer chromatography stick having a columnar or tubular support body not having a liquid permeability, and a first separating agent layer formed on a peripheral surface of the support body;

one or both of a second columnar body having an optical responsivity which is different from that of the component, and a liquid permeability, and a second thin layer chromatography stick having a columnar or tubular support body not having a liquid permeability and a second separating agent layer formed on the peripheral surface of the support body; and a connecting element that connects the first columnar body or the first thin layer chromatography stick to the second columnar body or the second thin layer chromatography stick so that the liquid permeates freely therethrough, wherein the first separating agent layer has the separation ability and optical responsivity which is the same as that of the component, and a liquid permeability, and the second separating agent layer has an optical responsivity different from that of the component and a liquid permeability.

18. The separation/detection kit according to claim 17, wherein the second columnar body and the second separating agent layer do not have the separation ability.

19. The separation/detection kit according to claim 17, wherein the shape of the second columnar body is cylindrical, and the shape of the support body is cylindrical or cylindrical tubular.

20. The separation/detection kit according to claim 18, wherein the first columnar body and the first separating agent layer contain a separating agent for optical isomers, and the second columnar body and the second separating agent layer do not contain a separating agent for optical isomers.

21. The separation/detection kit according to claim 10, wherein the separating agent for optical isomers is a polysaccharide derivative.

22. The separation/detection kit according to claim 21, wherein the polysaccharide derivative is constituted by a polysaccharide and any of an aromatic ester group, aromatic carbamoyl group and aromatic ether group, which is partially or totally replaced with a hydroxyl group or amino group of the polysaccharide.

* * * * *